United States Patent
Liu

(10) Patent No.: US 9,665,954 B2
(45) Date of Patent: May 30, 2017

(54) METHOD FOR RECONSTRUCTING PET IMAGE USING GPU PARALLEL COMPUTING

(71) Applicants: ZHEJIANG UNIVERSITY, Hangzhou (CN); Huafeng Liu, Hangzhou (CN)

(72) Inventor: Huafeng Liu, Hangzhou (CN)

(73) Assignees: ZHEJIANG UNIVERSITY, Hangzhou (CN); Huafeng Liu, Hangzhou (CN)

( * ) Notice: Subject to any disclaimer, the term of this patent is extended or adjusted under 35 U.S.C. 154(b) by 67 days.

(21) Appl. No.: 14/583,091

(22) Filed: Dec. 24, 2014

(65) Prior Publication Data

US 2015/0154767 A1 Jun. 4, 2015

Related U.S. Application Data

(63) Continuation-in-part of application No. PCT/CN2013/076794, filed on Jun. 5, 2013.

(30) Foreign Application Priority Data

Jun. 27, 2012 (CN) .......................... 2012 1 0213765

(51) Int. Cl.
*G06T 11/00* (2006.01)
*G06T 1/20* (2006.01)
(Continued)

(52) U.S. Cl.
CPC ............ *G06T 11/008* (2013.01); *A61B 6/037* (2013.01); *A61B 6/5205* (2013.01); *G06T 1/20* (2013.01);
(Continued)

(58) Field of Classification Search
CPC ..... A61B 6/037; A61B 6/5205; A61B 6/4258; G06T 11/006; G06T 1/20; G06T 11/008;
(Continued)

(56) References Cited

U.S. PATENT DOCUMENTS

2011/0182491 A1* 7/2011 Levin .................... G06T 11/006
382/131

FOREIGN PATENT DOCUMENTS

CN 102184559 A * 9/2011

OTHER PUBLICATIONS

Yu et al. "PET Image Reconstruction: GPU-accelerated Particle Filter Framework." 18th IEEE International Conference on Image Processing, Sep. 11, 2011, pp. 417-410.*
(Continued)

*Primary Examiner* — Jon Chang
(74) *Attorney, Agent, or Firm* — Matthias Scholl, PC; Matthias Scholl

(57) ABSTRACT

A method for reconstructing a PET image using GPU parallel computing including the following steps: 1) sampling particles of each voxel and obtaining an intensity value of each particle of the voxel; 2) calculating a prior intensity value of the voxel, and calculating a weight value of each particle of the voxel corresponding to the intensity value of each particle; 3) resampling the intensity value and the weight value of the particle, and obtaining the resampled intensity value of the particle and the resampled weight value of the particle; 4) repeating step 2) and step 3) until the resampled intensity value of the particle is converged to a certain value; and 5) calculating the voxel value according to a true intensity value of the particle and a true weight value of the particle.

2 Claims, 2 Drawing Sheets

(51) Int. Cl.
  *A61B 6/03* (2006.01)
  *A61B 6/00* (2006.01)
(52) U.S. Cl.
  CPC ........... *G06T 11/006* (2013.01); *A61B 6/4258* (2013.01); *G06T 2207/10104* (2013.01); *G06T 2207/30004* (2013.01); *G06T 2210/41* (2013.01); *G06T 2211/428* (2013.01)
(58) Field of Classification Search
  CPC ....... G06T 2210/41; G06T 2207/10104; G06T 2207/30004; G06T 2211/428
  USPC ........................................................ 382/131
  See application file for complete search history.

(56) References Cited

OTHER PUBLICATIONS

Ahn et al. "GPU-based Fast Projection-backprojection Algorithm for 3-D PET Image Reconstruction." IEEE Nuclear Science Symposium and Medical Imaging Conference, Oct. 23, 2011, pp. 2672-2674.*
Dieckmann et al. "Strategies for Accelerating Forward and Backprojection in List-mode OSEM PET Reconstruction using GPUs." IEEE Nuclear Science Symposium Conference Record, Oct. 24, 2009, pp. 4110-4113.*
English translation of CN 102184559 A.*

* cited by examiner

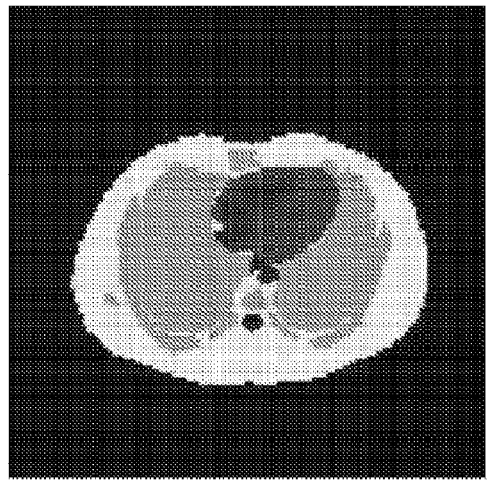
FIG. 2
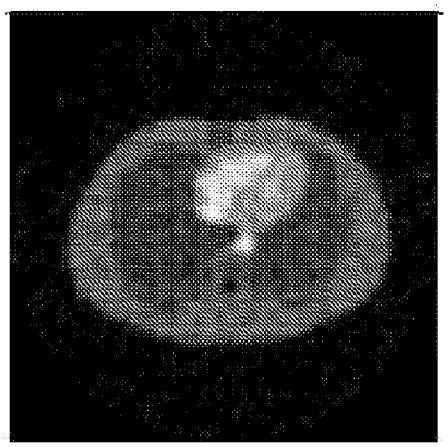 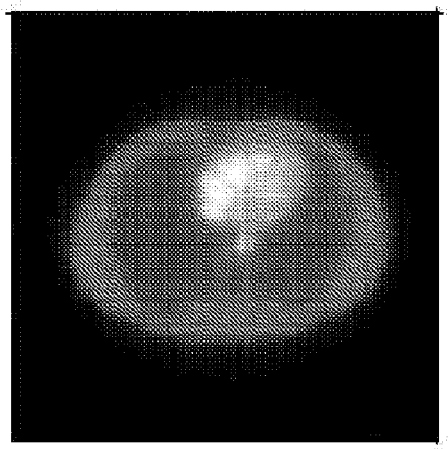
FIG. 3            FIG. 4

METHOD FOR RECONSTRUCTING PET IMAGE USING GPU PARALLEL COMPUTING

CROSS-REFERENCE TO RELATED APPLICATIONS

This application is a continuation-in-part of International Patent Application No. PCT/CN2013/076794 with an international filing date of Jun. 5, 2013, designating the United States, now pending, and further claims priority benefits to Chinese Patent Application No. 201210213765.4 filed Jun. 27, 2012. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The invention relates to the field of medical image processing, and more particularly to a method for reconstructing a Positron emission tomography (PET) image using graphics processing unit (GPU) parallel computing.

Description of the Related Art

PET image is usually reconstructed by using an analytical method, an iterative method, and a state-space based method.

A typical analytical method is a filtered back-projection method (FBP). It uses the Fourier transform to obtain the original data from a projected data. However, this model doesn't follow the real situation of PET imaging. Furthermore, FBP method cannot suppress noise, which causes a low quality result.

A typical iterative method adopts a maximum likelihood-expectation maximum (ML-EM) algorithm and a maximum a posteriori (MAP) algorithm. The ML-EM algorithm estimates the intensity of each voxel using the maximum likelihood estimation method. In the MAP algorithm, the objective function is the posterior distribution of voxels' intensity. Each voxel's intensity value is obtained by finding the optimal solution of the posterior. Iterative methods rely on certain statistical model. However, there are a lot of factors that influence the quality of PET imaging, including physiological information, structural information and so on. Such information cannot be used in the iterative methods, which is a drawback of these methods.

A typical state-space based method is adapted to model the process of PET imaging and to merge statistical information, physiological information and structural information into the reconstruction algorithm. The quality of reconstructed image is much better than those of iterative methods and analytical methods. The existing algorithm of solving state-space model is Kalman filtering method. This method assumes that the distribution of observed data is Gaussian, while the distribution of PET data is Poisson. The quality of Kalman filtering's solution is not very high due to this mismatch.

Because of the large data size and complex reconstruction algorithms, a long time is required to reconstruct an image, which is unsuitable for clinical usage. The traditional CPU computing is very slow due to its serial computing. On the other hand, high parallel CPU computing requires a very expensive supercomputer, which is not always practical in commercial usage.

SUMMARY OF THE INVENTION

In view of the above-described problems, it is one objective of the invention to provide a method for reconstructing a PET image using GPU parallel computing. The method largely shortens the reconstruction time in the absence of scarifying the quality of reconstructed images.

To achieve the above objective, in accordance with one embodiment of the invention, there is provided a method for reconstructing a PET image using GPU parallel computing. The method comprises the following steps:

1) sampling particles of each voxel using a linear sampling method according to a probability range of a voxel value, and obtaining an intensity value of each particle of the voxel;
2) calculating a prior intensity value of the voxel using an FBP method according to coincidence counting vectors acquired from sampling, and calculating a weight value of each particle of the voxel corresponding to the intensity value of each particle using GPU parallel computing and estimation algorithm of the weight value of the particle according to the prior intensity value of the voxel and the intensity value of the particle;
3) resampling the intensity value and the weight value of the particle using GPU parallel computing, and obtaining the resampled intensity value of the particle and the resampled weight value of the particle;
4) repeating step 2), using the resampled intensity value of the particle as the intensity value of the particle in step 2), repeating step 2) and step 3) until the resampled intensity value of the particle is converged to a certain value, and defining the resampled intensity value of the particle and the corresponding resampled weight value thereof as a true intensity value of the particle and a true weight value of the particle; and
5) calculating the voxel value using GPU parallel computing according to the true intensity value of the particle and the true weight value of the particle.

In a class of this embodiment, the linear sampling method comprises dividing the entire probability range of the voxel value into (s−1) parts to acquire s node values, where s represents a sampling number and each node value corresponds to the intensity value of each particle of each voxel.

In a class of this embodiment, the estimation algorithm of the weight value of the particle adopts the following equations:

$$P(j, i) = \frac{D(i, j) \times \frac{x[j]}{\sum_{j=1}^{n} x[j]}}{\sum_{j=1}^{n} \left\{ D(i, j) \times \frac{x[j]}{\sum_{j=1}^{n} x[j]} \right\}}$$

$$w_{(k)}[j] = \sum_{i=1}^{m} \{y[i] \times P(j, i)\} - \sum_{i=1}^{m} \{D(i, j) \times x_{(k)}[j]\}$$

where x[j] is the prior intensity value of a jth voxel of the PET image, y[i] is an ith coincidence counting of the coincidence counting vector, D(i,j) is an element value at an ith row and a jth column of a system matrix, $x_{(k)}[j]$ is the intensity value of a kth particle of a jth voxel of the PET image, $w_{(k)}[j]$ is a weight value of the kth particle of the jth voxel corresponding to $x_{(k)}[j]$, i, j, and k are all natural numbers, $1 \le i \le m$, $1 \le j \le n$, $1 \le k \le s$, m is a dimension of the coincidence counting vector, and n is a number of voxels of the PET image.

The system matrix D is an m×n matrix. The system matrix D, the coincidence counting vector y, and an intensity distribution vector x of the PET image satisfy the following relation: $y = D_x + e$, where e is a measurement noise, the intensity distribution vector x of the PET image is an n-dimensional vector and each element of the n-dimensional vector corresponds to the voxel value of each voxel of the PET image, and the system matrix D relates to structure parameters and performance parameters of a photodetector for detecting photons.

In a class of this embodiment, in step (5), the voxel value of each voxel is calculated according to the following equation:

$$x^*[j] = \sum_{k=1}^{s} \{x^*_{(k)}[j] \times w^*_{(k)}[j]\}$$

where $x^*_{(k)}[j]$ is the true intensity value of a kth particle of a jth voxel of the PET image, $w^*_{(k)}[j]$ is the true weight value of the kth particle of the jth voxel corresponding to $x^*_{(k)}[j]$, and $x^*[j]$ is the voxel value of the jth voxel of the PET image.

In a class of this embodiment, the GPU parallel computing is as follows:
- in a multiplication or division operation between a vector and a scalar, each element of the vector is mapped into kernels to execute the multiplication or division operation between the element of the vector and the scalar in each kernel, where a number of the kernels is equivalent to a dimension number of the vector;
- in a multiplication operation between a matrix and a vector, each element of the vector and each element of the matrix are mapped into kernels to execute the multiplication operation between the element of the matrix and the corresponding element of the vector, where a number of the kernels is equivalent to a dimension number of the matrix, and elements of a same row of a resulting matrix are added;
- in a multiplication or division operation between a matrix and a scalar, each element of the matrix is mapped into kernels to execute the multiplication or division operation between each element of the matrix and the scalar in each kernel, where a number of the kernels is equivalent to a dimension number of the matrix; and
- in calculation of other equations, each kernel calculates one equation with different variable values, respectively.

Advantages according to embodiments of the invention are summarized as follows:

The method of the invention uses particle filtering method to reconstruct a PET image. It models the noise as Poisson distribution rather than Gaussian distribution, which is more suitable for PET data. The quality of reconstructed image is higher than those of the ML-EM method and FBP method. Meanwhile, GPU parallel computing is used to accelerate the reconstruction. Parallel computing converts serial operations into parallel operations, thereby largely reducing computational time. Thus, the reconstruction method is suitable for clinical usage.

BRIEF DESCRIPTION OF THE DRAWINGS

FIG. 2 is a schematic diagram of a Zubal-thorax-phantom model;

FIG. 3 is a reconstructed PET image of a Zubal-thorax-phantom using a method for constructing a PET image in accordance with one embodiment of the invention; and FIG. 4 is a reconstructed PET image of a Zubal-thorax-phantom using an ML-EM method.

DETAILED DESCRIPTION OF THE EMBODIMENTS

Figure 1:
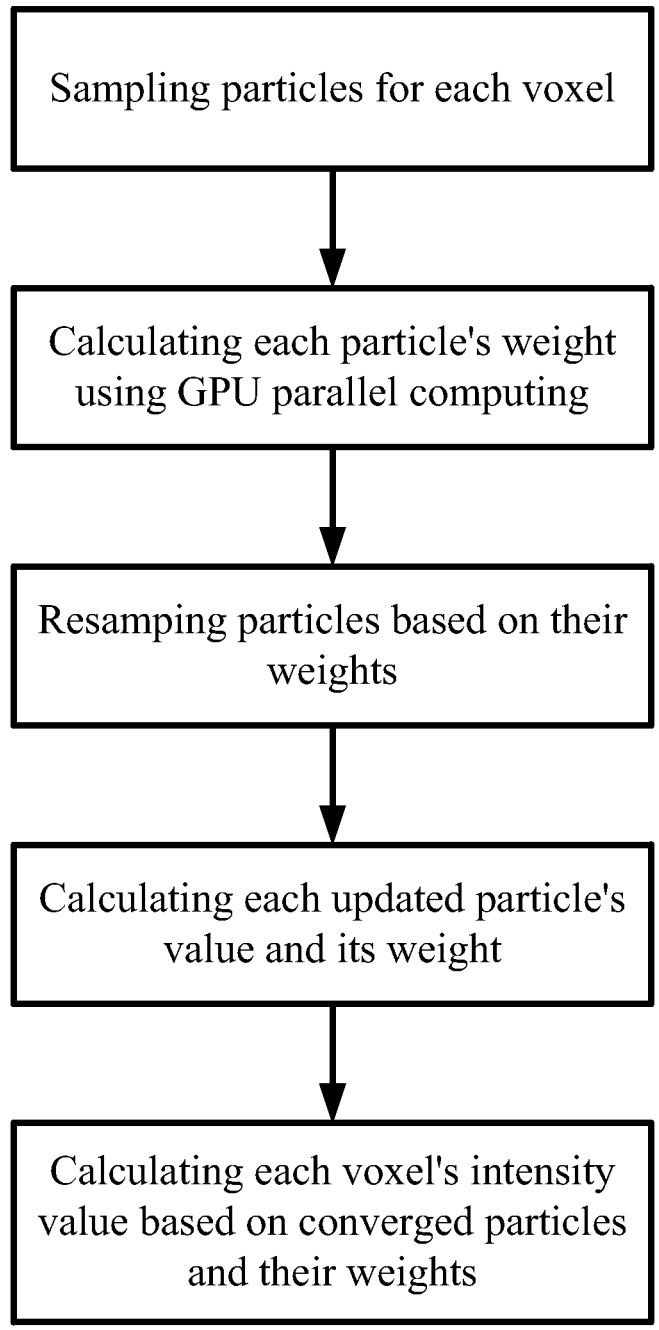
FIG. 1 is a flow chart of a method for reconstructing a PET image using GPU parallel computing in accordance with one embodiment of the invention.

For further illustrating the invention, experiments detailing a method for reconstructing a PET image using GPU parallel computing are described below. It should be noted that the following examples are intended to describe and not to limit the invention.

As shown in FIG. 1, the method for reconstructing the PET image using GPU parallel computing comprises the following steps:

1) Sampling Particles of Each Voxel

In accordance with a probability range of a voxel value, a linear sampling method is adopted to sample the particles of each voxel so that an intensity value of each particle of the voxel is obtained.

The linear sampling method first divides the entire probability range of the voxel value into (s−1) parts to acquire s node values, where s represents a sampling number and each node value corresponds to the intensity value of each particle of each voxel. In this embodiment, s=500.

2) Calculating a Weight Value of the Particle Using GPU Parallel Computing

First, an FBP method is utilized to calculate a prior intensity value of the voxel according to coincidence counting vectors acquired from sampling.

Second, according to a PET imaging principle, a state-space model of the PET image is expressed as follows:

$$\begin{cases} y = D_x + e \\ x_{t+1} = Ax_t \end{cases}$$

where D represents an m×n system matrix and relates to structure parameters and performance parameters of a photodetector for detecting photons, y represents a coincidence counting vector obtained from sampling and is an m-dimensional vector, x represents an n-dimensional intensity distribution vector of the PET image and each element of x corresponds to the voxel value of each voxel of the PET image, e represents a measurement noise, $x_{t+1}$ represents an intensity distribution vector of the PET image of a (t+1)th frame, $x_t$ represents an intensity distribution vector of the PET image of a tth frame, and A represents a state matrix.

According to the state-space equation of the PET image, equation expressions of an estimation algorithm of the weight value of the particle are established as follows:

$$P(j, i) = \frac{D(i, j) \times \frac{x[j]}{\sum_{j=1}^{n} x[j]}}{\sum_{j=1}^{n} \left\{ D(i, j) \times \frac{x[j]}{\sum_{j=1}^{n} x[j]} \right\}}$$

$$w_{(k)}[j] = \sum_{i=1}^{m} \{y[i] \times P(j, i)\} - \sum_{i=1}^{m} \{D(i, j) \times x_{(k)}[j]\}$$

where x[j] is the prior intensity value of a jth voxel of the PET image, y[i] is an ith coincidence counting of the coincidence counting vector, D(i,j) is an element value at an ith row and a jth column of a system matrix, $x_{(k)}[j]$ is the intensity value of a kth particle of a jth voxel of the PET image, $w_{(k)}[j]$ is a weight value of the kth particle of the jth voxel corresponding to $x_{(k)}[j]$, i, j, and k are all natural numbers, $1 \leq i \leq m$, $1 \leq j \leq n$, $1 \leq k \leq s$, m is a dimension of the coincidence counting vector, and n is a number of voxels of the PET image.

Finally, according to the prior intensity value of the voxel and the intensity value of the particle, the GPU parallel computing and the estimation algorithm of the weight value of the particle are utilized to calculate the weight value of each particle of the voxel corresponding to the intensity value of each particle.

A plurality of calculations of matrixes and vectors are involved in this step. Because of the large quantity of calculation and high parallel degree, the GPU parallel computing is adapted to accelerate these calculations, and strategies of the GPU parallel computing are as follows:

- in a multiplication or division operation between a vector and a scalar, each element of the vector is mapped into kernels to execute the multiplication or division operation between the element of the vector and the scalar in each kernel, where a number of the kernels is equivalent to a dimension number of the vector;

- in a multiplication operation between a matrix and a vector, each element of the vector and each element of the matrix are mapped into kernels to execute the multiplication operation between the element of the matrix and the corresponding element of the vector, where a number of the kernels is equivalent to a dimension number of the matrix, and elements of a same row of a resulting matrix are added;

- in a multiplication or division operation between a matrix and a scalar, each element of the matrix is mapped into kernels to execute the multiplication or division operation between each element of the matrix and the scalar in each kernel, where a number of the kernels is equivalent to a dimension number of the matrix; and

- in calculation of other equations, each kernel calculates one equation with different variable values, respectively.

3) Resampling the Particles

The intensity value and the weight value of the particle are resampled using GPU parallel computing, and the resampled intensity value of the particle and the resampled weight value of the particle are acquired.

A resampling algorithm is illustrated as follows using pseudo code:

```
a) building a cumulative distribution function (CDF) for each particle:
   c_1 = 0, c_i = c_{i-1} + w_k^i
b) randomly picking a number from a uniform distribution U[0, N_s^{-1}]
c) for j=1:N
   u_j = u_1 + N_s^{-1}(j - 1)
   while u_j > c_i
   *i = I + 1
   end while
   resampling: x_k^{j*} = x_k^i
   end for
```

Particles of large weight values are kept while particles of small weight values are deleted in the resampling process, so that the entire particle distribution is much closer to a true distribution. And results within a certain accuracy range are acquired after several iterations.

Because that all particles of the same voxel are required to be used sequentially, that is, a sequential relation exists between different particles; the resampling of the particles of the same voxel cannot be parallel calculated. Therefore, the strategy of the GPU parallel computing is to parallel the resampling of the particles of different voxels to one another, that is, the resampling algorithm of one voxel is correspondingly executed in one kernel.

4) Calculating a True Intensity Value of the Particle and a True Weight Value of the Particle Step 2) is repeated, the resampled intensity value of the particle is used as the intensity value of the particle in step 2). Step 2) and step 3) are repeated until the resampled intensity value of the particle is converged to a certain value. The resampled intensity value of the particle and the corresponding resampled weight value thereof are defined as the true intensity value of the particle and the true weight value of the particle, respectively.

5) Calculating a Voxel Value of Each Voxel

According to the true intensity value of the particle and the true weight value of the particle, the voxel value of each voxel of the PET image is calculated using GPU parallel computing via the following equations:

$$x^*[j] = \sum_{k=1}^{s} \{x^*_{(k)}[j] \times w^*_{(k)}[j]\}$$

where $x^*_{(k)}[j]$ is the true intensity value of a kth particle of a jth voxel of the PET image, $w^*_{(k)}[j]$ is the true weight value of the kth particle of the jth voxel corresponding to $x^*_{(k)}[j]$, and $x^*[j]$ is the voxel value of the jth voxel of the PET image.

The parallel computing of this step is also to parallel voxel values of different voxels to one another, that is, the calculation of the voxel value of one voxel is correspondingly executed in one kernel.

Practicability and reliability of the method of the invention are demonstrated by experiments. FIG. 2 is the widely used modeling of Zubal-thorax-phantom, a scanning degree thereof is 180°, and 128 angles and 128 radius are collected, and a pixel of the finally formed image is 128×128. Comparisons of the constructed PET image of the Zubal-thorax-phantom modeling using the method disclosed in the invention and using an ML-EM method are made. It is known from FIG. 3 that both an image resolution and an image definition constructed using the method of the invention are higher than those constructed using the ML-EM method. For the purpose of statistically analyzing the advantages of the method of the invention, Table 1 lists deviations and standard deviations of the image constructed by the method of the invention and by the ML-EM method in conditions of adding 10%, 20%, 30%, and 40% of noise to the original sonogram (coincidence counting vector).

TABLE 1

| Noise level | Reconstruction method | Deviation | Stand deviation |
|---|---|---|---|
| 10% | Particle filtering with GPU | 0.0056 | 0.1687 |
| | parallel computing ML-EM | 0.0111 | 0.0770 |
| 20% | Particle filtering with GPU | 0.1475 | 0.0685 |
| | parallel computing ML-EM | 0.1915 | 0.0873 |
| 30% | Particle filtering with GPU | 0.1746 | 0.0739 |
| | parallel computing ML-EM | 0.2174 | 0.1030 |
| 40% | Particle filtering with GPU | 0.2175 | 0.0986 |
| | parallel computing ML-EM | 0.2333 | 0.1103 |

It is known From Table 1 that the method disclosed in the invention is obviously superior to the EL-EM method of the prior art in both the deviation and the standard deviation, that is, compared with the existing construction method, the reliability of the static PET image reconstruction method based on the particle filter is demonstrated.

PET reconstruction methods realized by the GPU parallel computing of the invention and by the conventional CPU serial computing are further compared, and speed differences thereof are listed in Table 2.

TABLE 2

| Sinogram size | GPU parallel computing time (s) | CPU series computing time (s) | Acceleration ratio |
|---|---|---|---|
| 32 × 32 | 0.1850 | 23.4804 | 126.9211 |
| 64 × 64 | 0.3730 | 245.1592 | 657.263 |
| 128 × 128 | 10.917 | 7610.6 | 697.133 |

As shown in Table 2, the GPU parallel computing largely shortens computational time for reconstruction. The GPU parallel computing adopts a single precision float. As shown in Table 3, compared with the series computing, the loss in precision (the deviation and the standard deviation) of the single precision reconstruction of the parallel computing is not large.

TABLE 3

| | Deviation | Stand deviation |
|---|---|---|
| GPU parallel computing | 0.0216 | 0.0931 |
| CPU serial computing | 0.0056 | 0.1687 |

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for reconstructing a PET image using graphics processing unit (GPU) parallel computing, the PET image comprising a plurality of voxels, each voxel of the plurality of voxels comprising a plurality of particles, the method comprising:

1) sampling the plurality of particles of each voxel using a linear sampling method according to a probability range of a voxel value, and obtaining an intensity value of each particle;
2) calculating a prior intensity value of each voxel using an FBP method according to coincidence counting vectors acquired from sampling, and calculating a weight value of each particle corresponding to the intensity value of each particle and estimation algorithm of the weight value of each particle according to the prior intensity value of the voxel and the intensity value of each particle;
3) resampling the intensity value and the weight value of each particle, and obtaining the resampled intensity value of each particle and the resampled weight value of each particle;
4) repeating 2), using the resampled intensity value of each particle as the intensity value of each particle in 2), repeating 2) and 3) until the resampled intensity value of each particle is converged to a certain value, and defining the resampled intensity value of each particle and the corresponding resampled weight value thereof as a true intensity value of each particle and a true weight value of each particle; and
5) calculating the voxel value according to the true intensity value of each particle and the true weight value of each particle;

wherein:
the GPU parallel computing comprises:
a) in a multiplication or division operation between a vector and a scalar, each element of the vector is mapped into kernels to execute the multiplication or division operation between the element of the vector and the scalar in each kernel, where a number of the kernels is equivalent to a dimension number of the vector;
b) in a multiplication operation between a matrix and a vector, each element of the vector and each element of the matrix are mapped into kernels to execute the multiplication operation between the element of the matrix and the corresponding element of the vector, where a number of the kernels is equivalent to a dimension number of the matrix, and elements of a same row of a resulting matrix are added;
c) in a multiplication or division operation between a matrix and a scalar, each element of the matrix is mapped into kernels to execute the multiplication or division operation between each element of the matrix and the scalar in each kernel, where a number of the kernels is equivalent to a dimension number of the matrix; and
d) in calculation of other equations, each kernel calculates one equation with different variable values, respectively;
2) requires setting a state-space model of the PET image according to the following equation:

$$\begin{cases} y = D_x + e \\ x_{t+1} = Ax_t \end{cases}$$

where D represents an m×n system matrix, y represents an m-dimensional coincidence counting vector obtained from sampling, x represents an n-dimensional intensity distribution vector of the PET image and each element of x corresponds to the voxel value of each voxel, e represents a measurement noise, $x_{t+1}$ represents an intensity distribution vector of the PET image of a $(t+1)^{th}$ frame, $x_t$ represents an intensity distribution vector of the PET image of a $t^{th}$ frame, A represents a state matrix, m is a dimension of the coincidence counting vector, and n is a number of voxels of the PET image;

the estimation algorithm of the weight value of each particle in 2) adopts the following equations:

$$P(j, i) = \frac{D(i, j) \times \frac{x[j]}{\sum_{j=1}^{n} x[j]}}{\sum_{j=1}^{n} \left\{ D(i, j) \times \frac{x[j]}{\sum_{j=1}^{n} x[j]} \right\}}$$

$$w_{(k)}[j] = \sum_{i=1}^{m} \{y[i] \times P(j, i)\} - \sum_{i=1}^{m} \{D(i, j) \times x_{(k)}[j]\}$$

where $x[j]$ is the prior intensity value of a $j^{th}$ voxel of the PET image, $y[i]$ is an $i^{th}$ coincidence counting of the coincidence counting vector, $D(i,j)$ is an element value at an $i^{th}$ row and a $j^{th}$ column of a system matrix, $x_{(k)}[j]$ is the intensity value of a $k^{th}$ particle of a $j^{th}$ voxel of the PET image, $w_{(k)}[j]$ is a weight value of the $k^{th}$ particle of the $j^{th}$ voxel corresponding to $x_{(k)}[j]$, and i, j, and k are natural numbers, $1 \leq i \leq m$, $1 \leq j \leq n$, $1 \leq k \leq s$;

in 5) the voxel value of each voxel is calculated according to the following equation:

$$x^*[j] = \sum_{k=1}^{s} \{x^*_{(k)}[j] \times w^*_{(k)}[j]\}$$

where $x^*_{(k)}[j]$ is the true intensity value of a $k^{th}$ particle of a $j^{th}$ voxel of the PET image and represents a voxel matrix, $w^*_{(k)}[j]$ is the true weight value of the $k^{th}$ particle of the $j^{th}$ voxel corresponding to $x^*_{(k)}[j]$ and represents a scalar, and $x^*[j]$ is the voxel value of the $j^t$ voxel of the PET image;

1), 3), and 4) are performed by using d) of the GPU parallel computing;

2) is performed by using a), b), and c) of the GPU parallel computing; and 5) is performed by using c) of the GPU parallel computing.

2. The method of claim 1, wherein the linear sampling method comprises dividing the entire probability range of the voxel value into (s−1) parts to acquire s node values, where s represents a sampling number and each node value corresponds to the intensity value of each particle of each voxel.

* * * * *